(12) United States Patent
Traincard et al.

(10) Patent No.: US 7,413,863 B2
(45) Date of Patent: Aug. 19, 2008

(54) IDENTIFICATION OF SUBSTANCES THAT INHIBIT NEMO OLIGOMERIZATION

(75) Inventors: Francois Traincard, Issy les Moulineaux (FR); Fabrice Agou, Paris (FR); Michel Veron, Paris (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 11/760,014

(22) Filed: Jun. 8, 2007

(65) Prior Publication Data

US 2008/0050763 A1    Feb. 28, 2008

Related U.S. Application Data

(60) Provisional application No. 60/811,770, filed on Jun. 8, 2006.

(51) Int. Cl.
*C12Q 1/68* (2006.01)
*A61K 38/00* (2006.01)
(52) U.S. Cl. ............................................. 435/6; 514/12
(58) Field of Classification Search .................. 435/6; 514/12
See application file for complete search history.

(56) References Cited

OTHER PUBLICATIONS

Agou et al., JBC, 279(52), 54248-54257, 2004.*

\* cited by examiner

*Primary Examiner*—Maryam Monshipouri
(74) *Attorney, Agent, or Firm*—Oblon, Spivak, McClelland, Maier & Neustadt, P.C.

(57) ABSTRACT

The present invention provides methods for screening for substances which inhibit the oligomerization of NEMO and/or IKK-related complexes and/or signaling pathways based on the interference with NEMO oligomerization.

18 Claims, 6 Drawing Sheets

SEQUENCE LISTING

```
<160> NUMBER OF SEQ ID NOS: 2

<210> SEQ ID NO 1
<211> LENGTH: 1989
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<223> OTHER INFORMATION: Human-CFP Fusion Nucleotide Sequence
<220> FEATURE:
<221> NAME/KEY: misc_feature
<222> LOCATION: (1)..(717)
<223> OTHER INFORMATION: CFP Sequence
<220> FEATURE:
<221> NAME/KEY: misc_feature
<222> LOCATION: (718)..(753)
<223> OTHER INFORMATION: Linker Sequence
<220> FEATURE:
<221> NAME/KEY: misc_feature
<222> LOCATION: (754)..(1989)
<223> OTHER INFORMATION: NEMO Sequence

<400> SEQUENCE: 1
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgacctg gggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacat cagccacaac gtctatatca ccgccgacaa gcagaagaac     480
ggcatcaagg ccaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtcc     720
ggactcagat ctcgagctca agcttcgaat tcgaacaagc acccctggaa gaaccagctg     780
agtgagatgg tgcagcccag tggtggccca gcagaggacc aggacatgct gggtgaagaa     840
tcttctctgg ggaagcctgc aatgctacat ctgccttcag agcagggtac tcctgagacc     900
ctccagcgct gcctggaaga gaatcaagag ctccgagacg ctatccggca gagcaatcag     960
```

```
atgctgaggg aacgctgtga ggagctgctg catttccagg tcagccagcg ggaggagaag    1020
gagttcctta tgtgcaaatt ccaggaagcc cggaagctgg tggagagact gagcttggag    1080
aagcttgatc ttcggagtca gagggaacag gccttaaagg agttggagca actgaagaaa    1140
tgccaacagc agatggctga ggacaaggcc tctgtgaaag ttcaggtgac atcattgctc    1200
ggagaactcc aggagagcca gagccgtttg gaggctgcca ccaaggatcg gcaagcttta    1260
gagggaagga ttcgagcagt tagtgagcag gtcagacagc tggagagtga gcgggaggtg    1320
ctacagcagc agcacagcgt ccaggtggac cagctgcgta tgcagaacca gagcgtggag    1380
gctgccttgc gaatggggcg gcaggctgct tcagaggaga gcggaagct ggctcagttg    1440 caggcagcct atcaccagct cttccaagac tacgacagcc acattaagag cagcaagggc    1500
atgcagctgg aagatctgag gcaacagctc cagcaagctg aggaggccct ggtagccaaa    1560
caggaattga ttgataagct gaaagaggag gctgagcagc acaagattgt gatggagact    1620
gtgccagtct tgaaggccca ggcggatatc tacaaggctg acttccaagc tgagaggcat    1680
gcccgggaga agctggtgga gaagaaggag tatttgcagg agcagctgga gcagctgcag    1740
cgcgagttca acaagctgaa agttggctgc atgagtcag ccaggattga ggatatgagg    1800
aagcggcatg tagagactcc ccagcctact ttactccctg ctccagctca ccactccttt    1860
catttggcct tgtccaacca gcggaggagc cctcctgaag aacctcctga cttctgttgt    1920
ccgaagtgcc agtatcaggc tcctgatatg gacactctac agatacatgt catggagtgc    1980
atagagtag                                                            1989

<210> SEQ ID NO 2
<211> LENGTH: 1989
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<223> OTHER INFORMATION: Human-YFP Fusion Nucleotide Sequence
<220> FEATURE:
<221> NAME/KEY: misc_feature
<222> LOCATION: (1)..(717)
<223> OTHER INFORMATION: YFP Sequence
<220> FEATURE:
<221> NAME/KEY: misc_feature
<222> LOCATION: (718)..(753)
<223> OTHER INFORMATION: Linker Sequence
<220> FEATURE:
<221> NAME/KEY: misc_feature
<222> LOCATION: (754)..(1989)
<223> OTHER INFORMATION: NEMO Sequence

<400> SEQUENCE: 2
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttcggcta cggcctgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
```

-continued

```
gaccactacc agcagaacac ccccatcggc gacggccccg tgctgctgcc cgacaaccac    600
tacctgagct accagtccgc cctgagcaaa gacccaacg agaagcgcga tcacatggtc     660
ctgctggagt tcgtgaccgc cgccgggatc actctcggca tggacgagct gtacaagtcc   720
ggactcagat ctcgagctca agcttcgaat tcgaacaagc acccctggaa gaaccagctg    780
agtgagatgg tgcagcccag tggtggccca gcagaggacc aggacatgct gggtgaagaa     840
tcttctctgg ggaagcctgc aatgctacat ctgccttcag agcagggtac tcctgagacc    900
ctccagcgct gcctggaaga gaatcaagag ctccgagacg ctatccggca gagcaatcag    960
atgctgaggg aacgctgtga ggagctgctg catttccagg tcagccagcg ggaggagaag    1020
gagttcctta tgtgcaaatt ccaggaagcc cggaagctgg tggagagact gagcttggag    1080
aagcttgatc ttcggagtca gagggaacag gccttaaagg agttggagca actgaagaaa    1140
tgccaacagc agatggctga ggacaaggcc tctgtgaaag ttcaggtgac atcattgctc    1200
ggagaactcc aggagagcca gagccgtttg gaggctgcca ccaaggatcg gcaagcttta    1260
gagggaagga ttcgagcagt tagtgagcag gtcagacagc tggagagtga gcggaggtg    1320 ctacagcagc agcacagcgt ccaggtggac cagctgcgta tgcagaacca gagcgtggag    1380
gctgccttgc gaatggggcg gcaggctgct tcagaggaga agcggaagct ggctcagttg    1440
caggcagcct atcaccagct cttccaagac tacgacagcc acattaagag caacaagggc    1500
atgcagctgg aagatctgag gcaacagctc cagcaagctg aggaggccct ggtagccaaa    1560
caggaattga ttgataagct gaaagaggag gctgagcagc acaagattgt gatggagact    1620
gtgccagtct tgaaggccca ggcggatatc tacaaggctg acttccaagc tgagaggcat    1680
gcccgggaga agctggtgga gaagaaggag tatttgcagg agcagctgga gcagctgcag    1740
cgcgagttca acaagctgaa agttggctgc catgagtcag ccaggattga ggatatgagg    1800
aagcggcatg tagagactcc ccagcctact ttactccctg ctccagctca ccactccttt    1860
catttggcct tgtccaacca gcggaggagc cctcctgaag aacctcctga cttctgttgt    1920
ccgaagtgcc agtatcaggc tcctgatatg gacactctac agatacatgt catggagtgc    1980
atagagtag                                                            1989
```

US 7,413,863 B2

IDENTIFICATION OF SUBSTANCES THAT INHIBIT NEMO OLIGOMERIZATION

CROSS-REFERENCE TO RELATED APPLICATIONS

The present application claims the benefit of U.S. provisional application 60/811,770 filed Jun. 8, 2006.

BACKGROUND OF THE INVENTION

1. Field of the Invention

The present invention provides methods for screening for substances which inhibit the oligomerization of NEMO and/or IKK-related complexes and/or signaling pathways based on the interference with NEMO oligomerization.

2. Description of the Background

NF-κB plays a prominent role in the inducible expression of genes involved in processes like immune and inflammatory responses, cell growth and death, oncogenesis (Hayden, M. S. and Ghosh, S. (2004) *Genes Dev*, 18, 2195-2224). In resting cells, NF-κB is sequestered in the cytoplasm through interaction with inhibitory proteins known as IκBs (Baldwin, A. S., Jr. (1996) *Annu Rev Immunol*, 14, 649-683). Stimuli transducing through the TNF, Toll-like, IL-1, B and T cell receptors as well as the HTLV-1 Tax protein promote IκB phosphorylation by IκB kinases (IKK), ubiquitination and degradation. This allows NF-κB to translocate into the nucleus where it activates gene transcription (Karin, M. and Ben-Neriah, Y. (2000) *Annu Rev Immunol*, 18, 621-663). IKK activation proceeds from outside the cell to the cytoplasm, but it can also occur from the nucleus to the cytoplasm (Wu et al (2006a) *Nat Cell Biol*). The NF-κB signaling cascade can be triggered through a <<classical>> or an <<alternative>> pathway (Bonizzi, G. and Karin, M. (2004) *Trends Immunol*, 25, 280-288). Unlike most proinflammatory stimuli which lead to transient increase in IKK activity, the oncoprotein Tax leads to a persistent activation of IKKs through both pathways (Sun, S. C. and Yamaoka, S. (2005) *Oncogene*, 24, 5952-5964).

In the classical pathway, IKK activity is associated with a multiprotein complex composed of two serine/threonine kinases, IKKα and IKKβ (Zandi et al (1997) *Cell*, 91, 243-252) and a non catalytic protein, NEMO (NF-κB essential modulator) (Yamaoka, S et al (1998) *Cell*, 93, 1231-1240). Cells lacking NEMO are unable to assemble the IKK complex and exhibit severe defects in NF-κB activation. The mechanism by which the IKK complex is activated remains unclear: trans-autophosphorylation (Tang et al (2003) *J Biol Chem*, 278, 37297-37305) as well as kinases such as MEKK3 (Yang et al (2001) *Nat Immunol*, 2, 620-624) or TAK1 (Takaesu et al (2003) *J Mol Biol*, 326, 105-115) have been implicated. Recently, the first genetic evidence that TAK1 was essential for TNFα and IL-1 NF-κB activation (Sato et al (2005) *Nat Immunol*, 6, 1087-1095) was published. Besides, converging evidence suggests that NEMO oligomerization also plays a crucial role in the IKK complex activation (Inohara et al., (2000) *J Biol Chem* 275, 27823-27831; Poyet et al (2000) *J Biol Chem*, 275, 37966-37977). The subunit composition and stoichiometry of the IKK complex is still debated although many reports suggest an association between the IKKα/IKKβ heterodimer and NEMO.

SUMMARY OF THE INVENTION

Accordingly, one object of the present invention is to provide nucleic acid molecules encoding a full length NEMO polypeptide and/or at least a portion of the C-terminal oligomerization domain of NEMO and at least fluorescent protein as well as a cell containing the nucleic acid molecules. The C-terminal domain is composed of the minimal oligomerization domain including two sucessives coiled-coil motifs, CC2 (residues 246-286) and LZ (residues 390-412) (Tegethoff, 2003, Mol. Cell Biol.;Traincard, 2003, J. Biol. Chem. submitted), and a zinc finger motif at the extremity of the C-terminus. In a particular embodiment, the invention provides a nucleic acid molecule encoding the portion of the C-terminal oligomerization domain of NEMO encompassing the two sequences CC- and LZ. and at least fluorescent protein.

Another object is to provide methods for identifying substances which can be useful for the treatment of diseases or studying physiological mechanisms in which NFκ-B plays a prominent role, such as immune and inflammatory responses, cell growth and de9ath and oncogenesis.

Another object of the present invention is to provide a method of identifying a substance which inhibits NFκ-B Essential Modulator (NEMO) oligomerization, by providing a cell deficient in endogenous NEMO and which is transformed with one or more polynucleotides that express at least two peptides that comprise a NEMO oligomerization region or transforming a cell with such polynucleotides; applying the substance to the cell; and analyzing the level of oligomerization of the peptides that comprise a NEMO oligomerization region compared to the level of oligomerization of the peptides in the absence of the substance, wherein a reduction of oligomerization of the peptides in the presence of the substance indicates that the substance inhibits NEMO oligomerization.

Another object of the present invention is to provide a method of identifying a substance which inhibits IKK complex formation or activation [The complex can be formed, but not followed by its activation, both kind of compounds: those altering the formation and those altering the activation could be interesting and useful], comprising providing a cell deficient in endogenous NEMO and which is transformed with one or more polynucleotides that express at least two peptides that comprise a NEMO oligomerization region or transforming a cell with the polynucleotides; applying the substance to the cell; and analyzing the level of IKK complex formation compared to the level of IKK complex formation in the absence of the substance, wherein a reduction of IKK complex formation in the presence of the substance indicates that the substance inhibits IKK complex formation.

Another object of the present invention is to provide a method of identifying a substance which inhibits NFκ-B Essential Modulator (NEMO) oligomerization and/or which inhibits IKK complex formation or activation, by providing a system in which at least two NEMO polypeptides are provided and in which the NEMO polypeptides are capable of oligomerization, applying the substance to the system; and analyzing the level of oligomerization of the peptides that comprise a NEMO oligomerization region compared to the level of oligomerization of the peptides in the absence of the substance, wherein a reduction of oligomerization of the peptides in the presence of the substance indicates that the substance inhibits NEMO oligomerization.

Another object of the present invention is to provide substances that are identified by the above-methods and, further to their use to inhibit NFκ-B and to treat disease in which NFκ-B plays a prominent role.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
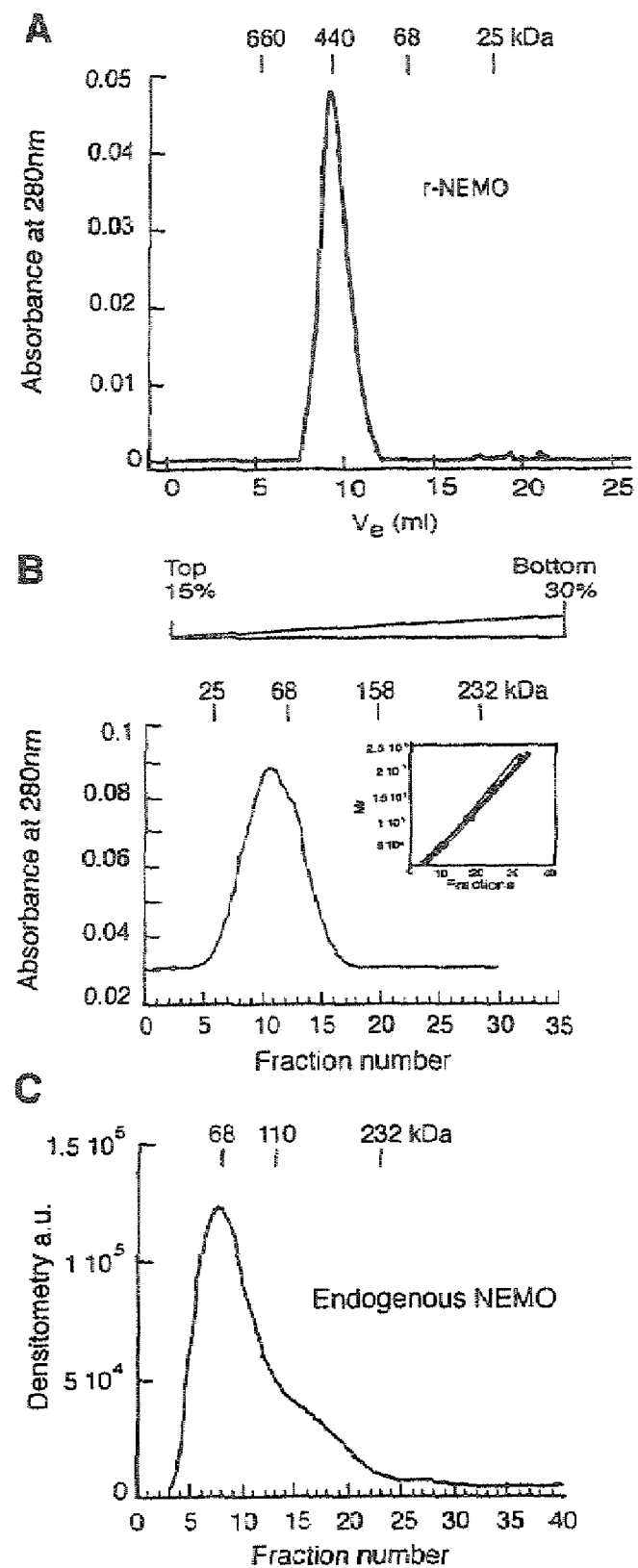
FIG. 1: rNEMO behaviour in gel filtration and glycerol gradient. 280 nm detection of rNEMO either A. chromatographed over a Superdex 200 HR gel filtration column or B. ultracentrifugated through a 15-30% linear glycerol gradient. Inset: Mr calibration curves of five independent gradients. C. Densitometric quantification of Western blot (WB) detected NEMO protein in fractions from cytosolic Ikkα$^{-/-}$ Ikkβ$^{-/-}$ MEF cell extracts submitted to glycerol gradient. a.u.: arbitrary unit.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory, New York (1982) and Sambrook et al., Molecular Cloning: A Laboratory Manual, Cold Spring Harbor Laboratory, New York (1989) and the various references cited therein.

"Isolated" means separated out of its natural environment.

"Polynucleotide" in general relates to polyribonucleotides and polydeoxyribonucleotides, it being possible for these to be non-modified RNA or DNA or modified RNA or DNA.

The term "nucleotide sequence" as used herein means a polynucleotide molecule in the form of a separate fragment or as a component of a larger nucleic acid construct that has been derived from DNA or RNA isolated at least once in substantially pure form (i.e., free of contaminating endogenous materials) and in a quantity or concentration enabling identification, manipulation, and recovery of its component nucleotide sequences by standard biochemical methods. Such sequences are preferably provided in the form of an open reading frame uninterrupted by internal non-translated sequences, or introns that are typically present in eukaryotic genes. Sequences of non-translated DNA may be present 5' or 3' from an open reading frame where the same do not interfere with manipulation or expression of the coding region.

The term "nucleic acid molecule" as used herein means RNA or DNA, including cDNA, single or double stranded, and linear or covalently closed molecules. A nucleic acid molecule may also be genomic DNA corresponding to the entire gene or a substantial portion therefor to fragments and derivatives thereof. The nucleotide sequence may correspond to the naturally occurring nucleotide sequence or may contain single or multiple nucleotide substitutions, deletions and/or additions including fragments thereof. All such variations in the nucleic acid molecule retain the ability to encode a biologically active enzyme when expressed in the appropriate host or an enzymatically active fragment thereof. The nucleic acid molecule of the present invention may comprise solely the nucleotide sequence encoding an enzyme or may be part of a larger nucleic acid molecule that extends to the gene for the enzyme. The non-enzyme encoding sequences in a larger nucleic acid molecule may include vector, promoter, terminator, enhancer, replication, signal sequences, or non-coding regions of the gene.

"Polypeptides" are understood as meaning peptides or proteins which comprise two or more amino acids bonded via peptide bonds.

As used herein, a substance that can be identified and/or screened by the methods described herein include biological macromolecules, such as polypeptides, peptides, nucleic acids, antibodies, and carbohydrates, and other chemical organic molecules. Combinations of substances for their joint effect at achieving the goals of the present invention can also be used.

As used herein, the term "reduced" or "inhibited" in relation to enzymatic activity means decreasing the intracellular activity of one or more enzymes in the NF-κB pathway either directly or indirectly and/or that inhibits IKK complex formation or activation. The phrase "inhibiting the NF-κB pathway" preferably means that the NF-κB pathway is inhibited by alteration of NEMO oligomerization.

Cells activate a large variety of genes implicated in the inflammatory and immune responses, and in apoptosis and cell growth In response to a large variety of stimuli such as pro inflammatory cytokines (TNF-alpha and IL-1) or bacterial lipopolysaccharide (LPS). Most of these genes are controlled by NF-κB transcription factors whose activation is modulated by a specific high molecular weight complex composed of two protein kinases named IKK-alpha and IKK-beta associated with a modulator and regulatory protein called NEMO (NF-κB Essential Modutator/IKK gamma). NEMO is essential as nemo –/–fibroblasts or lymphocytes cannot respond to a wide variety of NF-κB activating stimuli. NF-kB activation by several stimuli requires NEMO oligomerization.

The invention provides a method of identifying a substance which inhibits NFκ-B Essential Modulator (NEMO) oligomerization and/or that inhibits IKK complex formation or activation, by providing a cell deficient in endogenous NEMO and which is transformed with one or more polynucleotides that express at least two peptides that comprise a NEMO oligomerization region or transforming a cell with such polynucleotides; applying the substance to the cell; and analyzing the level of oligomerization of the peptides that comprise a NEMO oligomerization region compared to the level of oligomerization of the peptides in the absence of the substance, wherein a reduction of oligomerization of the peptides in the presence of the substance indicates that the substance inhibits NEMO oligomerization.

The oligomerization domain of NEMO has been identified (Agou et al., 2004, J. Biol. Chem., 279,27861) and peptides mimicking this domain display inhibitory properties on the NF-κB pathway have been described (Agou et al, 2004, J. Biol Chem., 279,54248, and U.S. application Ser. No. 10/948,649, which is incorporated herein by reference) that block the inflammatory response and killing cancer cells. In one embodiment, at least two peptides, polypeptides or proteins having the same oligomerization domain can be used. In another embodiment, the at least two polypeptides, peptides, or proteins have different binding domains provided that the different binding domains can cause the interaction between the NEMO peptides, polypeptides or proteins and/or facilitate the formation of IKK complexes and/or mediate NFκ-B mediated signaling. Compounds to be detected are "activators", but it will be also possible to reduce the formation of IKK complex, then inhibitors will be identified.

Examples of NEMO proteins are those encoded by the nucleotides 754 to 1989 of SEQ ID NO:1 or SEQ ID NO:2 (SEQ ID NO:1 and 2 are the regions of the plasmids of pECFP-NEMO and pEYFP-NEMO described further below in the Examples section containing the coding sequence for the hybrid fluorescent/NEMO protein). In another embodiment, the NEMO that can be used are those that are encoded by polynucleotide sequence with at least 70%, preferably 80%, more preferably at least 90, 95, 97, 98 and/or 99% identity to the NEMO coding sequence within nucleotides 754 to 1989 of SEQ ID NO:1 and/or 2 and which mediate oligomerization. These homologous polynucleotides can hybridize under stringent conditions to those NEMO nucleic acid sequences. The terms "stringent conditions" or "stringent hybridization conditions" includes reference to conditions under which a polynucleotide will hybridize to its target sequence, to a detectably greater degree than other sequences (e.g., at least 2-fold over background) And can include hybridization in 50% formamide, 1 M NaCl, 1% SDS at 37° C., and a wash in 0.1×SSC at 60 to 65° C. (see Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel, et al., Eds., Greene Publishing and Wiley-Interscience, New York (1995)). Amino acid and polynucleotide identity, homology and/or similarity can be determined using the ClustalW algorithm, MEGALIGN™, Lasergene, Wis.)

Preferably the methods described herein utilize cells, preferably mammalian, and more preferably human cells that are deficient in endogenous nemo (i.e., do not express NEMO protein from the endogenous chromosome, which is different from exogenously introduced nucleic acid coding regions that may reside episomally or have been integrated into the chromosome).

The cells are transformed with one or more nucleic acid molecules that encode at least a region of the NEMO protein that forms oligomers and/or mediates IKK complex formation. In one preferred embodiment, a nucleotide sequence encoding the whole NEMO protein is used. In another preferred embodiment, a partial NEMO sequence is used, containing the C-terminal portion comprising the oligomerization region. Introducing nucleic acid molecules into cells is a well-known technique; reference being made to the general methodology textbooks described hereinabove and otherwise known in this field. In one embodiment, these nucleic acid molecules are contained within and can be provided in a vector.

Preferably the vector is an expression vector. Typically an expression vector is one that places the nucleic acid encoding a particular protein or polypeptide under the direct transcriptional control of a promoter that is either constitutive or inducible (i.e., causes expression in response to certain stimuli such as heat or chemicals). This expression vector may be engineered to self-replicate in the cell thereby maintaining it as an episome (but may also be incorporated into one or more chromosomes of the cell. In addition or alternatively, the vector may be engineered to direct recombination into the cellular chromosomal material, and preferably engineered to direct site-specific recombination. Appropriate selectable markers as known in this field can be used. Preferable vectors are, for example, lentiviral vectors, in particular those encompassing the triplex sequence, as those disclosed in the U.S. Pat. No. 6,682,907 patent and in WO 99-55892 international PCT application which are incorporated here by reference.

Levels of expression from the vector can be determined by measuring changes in transcript levels, e.g., using Northern blots, dot-blots, primer extensions, RNase protections, RT-PCR and the like. Such methodologies are well-known in this field. Likewise, assessing protein expression, protein complexes are known in the field.

The substances to be tested can be brought into contact with the NEMO molecules in a test involving their membrane permeability whereby the substances are brought into contact with cells containing the NEMO proteins prior to their lysis. Additionally or alternatively, naive cell extracts or cell extracts treated with NFκB channel activators can be used. Additionally or alternatively, the oligomerization can be reconstituted ex cellulo and the testing can be performed in the reconstituted system.

To test a particular substance on the cell, generally, the substance can be simply added to the culture medium or to the cells directly having removed the culture medium from the cells for a time to allow the application of the test substance. If the cells are not provided in a culture medium but a buffered solution that are known in this field, e.g., phosphate buffered saline or Tris-buffered saline, the substance can be added directly to the solution.

The substance can be added in the form of a lyophilized powder or as deemed appropriate in a proper biologically acceptable carrier solution, such as buffered saline or water.

The oligomerization of NEMO can be analyzed by conventional protein methods and preferably, to simplify the analysis, use one or more detectable moieties. In one aspect, the at least two NEMO molecules have different detectable moieties.

Techniques using FRET (Fluorescence Resonance Energy Transfer)-based fluorescent labels (Patterson et al (2000) *Anal. Biochem* 284, 438) and, preferably proteins which fluoresce under different wavelengths may also be employed. Examples of known fluorescent proteins include, green fluorescent protein (GFP), cyan fluorescent protein (CFP), yellow fluorescent protein (YFP) and others described in Shaner et al (2004) (*Nat. Biotech* 22:1567). Other fluorophore that can be used include CFP/ds Red and/or GFP/ds Red (Erickson et al (2003) *Biophys J*, vol. 85:599-611) and Cyan variants of the orange type (Karawawa et al, *Biochem J.* 2004 Jul. 1;381(Pt 1):307-12) In this embodiment of using fluorescent proteins, it is preferred that a hybrid construct is used such that the NEMO molecule is linked, either directly or through a linker molecule (e.g., a short peptide), to the fluorescent protein. The linkage can occur at the N-terminus or C-terminus of the NEMO molecule, preferably provided that the added linkage does not interfere with NEMO oligomerization.

FRET measurements can be performed on cell extracts that have been transiently transfected with the appropriate expression vehicles and that have been treated with an NFκB channel activator. Alternatively, stably transformed cells can be used that express the NEMO proteins at physiological or non-physiological levels. The interaction between NEMO and substances that modulate its oligomerization can be detected by direct measurement of the FRET perturbation resulting from position two different fluorescent protein-NEMO proteins in proximity; measurement of the loss of fluorescence anisotropy resulting from hetero FRET; and/or measurement of the loss of fluorescence anisotropy resulting from homo FRET in the case in which a single fluorescent marker is used.

Determining and comparing NEMO oligomerization and indirectly the determination of the formation IKK complex may also be used for identifying substances that modulate NFκ-B mediated signaling. Such a method for identifying a substance that modulates these complexes and/or activities may include comparing the relative complex formation and/or activities in a cell that is deficient in NEMO before and after contacting the cell with a substance, and selecting a substance that modulates the complex formation and/or activities.

A comparison is made between a control sample of cell that has not been contacted with the substance being tested and a test sample of the same cell type exposed to the putative substance. The comparison can also assess the kinetic profile of the oligomerization of the NEMO oligomerization domains. For example, an agent that decreases NEMO oligomerization in a cell compared to the untreated control is indicative of an agent that may affect IKK complex formation and/or NFκ-B mediated activities.

In addition, high-throughput screening technology may also be employed to identify single or multiple substances. High throughput screening technology is commonly used to define the rapid processing of cells on a large scale. This method may comprise contacting multiple cells with multiple candidate substances and measuring the effects of those substances on a variety of cells compared to control cell lines. Thus, identifying substances on a large scale can be performed. For example, the methods described above can be applied on large scale to distinguish substances having different effects or magnitudes of effects on the oligomerization of NEMO peptides, endogenous NEMO oligomerization, NFκ-B formation, and NF-κ-B mediate signaling pathways.

The analysis of substances could be part of a multiplexing assay where other molecules/parameters are monitored simultaneously to provide a multi-sided biochemical signature of the effect the substance has on the cell and the formation of complexes and activities. In one embodiment of this combinatorial analysis, two or more parameters, such as NEMO protein or peptide oligomerization, IKK complex formation, and NFκ-B mediated signaling activities, are measured simultaneously or separately for a particular substance to identify a correlation between NEMO oligomerization, IKK complex formation, and NFκ-B mediated signaling activities.

In another embodiment, other signaling pathways, such as second messengers (including but not limited to cyclic AMP, protein kinases, and enzymes) and cellular parameters (including but not limited to cell morphology, viability, apoptosis, and organelle distribution) can be tested in combination to study the effects of the substances on these aspects as well.

Substances identified with the present methods may be formulated as compositions with a pharmaceutically acceptable excipient or carrier, or in combination with other anti-cancer drugs. Such substances or compositions may be administered by known routes, e.g. orally, parenterally, intravenously, intramuscularly, subcutaneously, or directly to the site of the cancer, to subjects having diseases characterized as having an NFκ-B signaling component. Formulation in general is described in Chapter 25.2 of Comprehensive Medicinal Chemistry, Volume 5, Editor Hansch et al, Pergamon Press 1990.

The dosages can be set up individually depending on the purpose of administration (prevention, maintenance (prevention of aggravation), alleviation (improvement of symptom) or cure); the kind of disease; the symptom, sex and age of patient; the administration method and the like and is not limited particularly.

The present invention also embodies kits for use in determining whether a substance has the effect of the methods described herein and can include, for example, cell samples; reagents for detecting oligomerization; and may also contain control substances known to have a specific inhibitory effect thereby enabling a comparison with the test substances. These kits can also contain detectable moieties, which may be a fluorescent label.

EXAMPLES

Example 1

In the following experiments, we reevaluated the molecular mass and the activity of the IKK complex in extracts from resting or Tax-activated cells by glycerol gradient ultracentrifugation since this method alleviates the problems encountered with NEMO in gel filtration. We also monitored a stimulus-dependent oligomerization of NEMO in living cells through FRET experiments.

Methods

Cell Culture and Transient Transfections

Rat-1, M319-5b (see supplementary data), 5R fibroblast and wild type, Ikkα$^{-/-}$Ikkβ$^{-/-}$ and Nemo$^{-/-}$ MEF cells were grown in Dulbecco's modified Eagle's medium supplemented with 10% fetal bovine serumn. For 5R cells, 20% 5R conditioned medium was added to fresh culture medium. Transfections using Fugene 6 (Roche) were performed according to the manufacturer protocol using, per well of a 6 well-plate, 2 μg of pECFP-Nemo or pEYFP-Nemo plasmid (single transfection) or 1 μg each (double transfection). For plasmid obtaining, see supplementary data. In NF-κB complementation assays 100 ng of pEF1-lacZ (marker for transfection efficiency) and Igκ-luciferase plasmids were added to the transfection mix. Cell fluorescence was controlled with an Axiovert 200 (Zeiss) inverted microscope one day after transfection.

NF-κB Complementation and Kinase Assays

Cells transfected with the lacZ and the Igκ-luciferase plasmids were trypsinated, pelleted and resuspended in fresh culture medium. Cell suspension was stimulated by IL-1β (BD, Biosciences, 10 ng/ml) or TNFα (BD Biosciences, 20 ng/ml) for 30 min at 37° C. They were washed in PBS buffer, resuspended in culture medium and incubated in plate for an additional 3.5 hr period at 37° C. Cells were lysed in 200 μl of cold FRET buffer (Tris-phosphate buffer pH 7.8 containing 8 MM $MgCl_2$, 1 mM DTE, 1 mM DDM, 10% glycerol and Roche protease inhibitors) and clarified by centrifugation (10,000 g, 30 min at 4° C.). Supernatants were tested for β-galactosidase (30 μl) (Detection kit II, BD Biosciences) and luciferase (70 μl) activity. Kinase activity in cytosolic extracts or glycerol gradient fractions was detected as described by Yamaoka, S., Courtois, G., Bessia, C., Whiteside, S. T., Weil, R., Agou, F., Kirk, H. E., Kay, R. J. and Israel, A. (1998) Complementation cloning of NEMO, a component of the IkappaB kinase (IKK) complex essential for NF-kappaB activation. *Cell*, 93, 1231-1240.

Gel Filtration Analysis and Glycerol Gradient Ultracentrifugation

Gel filtration analysis was performed as previously described (Agou, F., Ye, F., Goffinont, S., Courtois, G., Yamaoka, S., Israel, A. and Veron, M. (2002) NEMO trimerizes through its coiled-coil C-terminal domain. *J Biol Chem*, 277, 17464-17475). For glycerol gradient experiments, $10^8$ cells were treated with 200 μl cold lysis buffer (Yamaoka et al (1998) *Cell*, 93, 1231-1240) and centrifugated at 100,000 g for 1 hr at 4° C. 15%-30% linear glycerol gradients were prepared in lysis buffer using the Gradient Master (Biocomp, Serlabo), then rotated at a pre-set angle of 85° (20 rpm, 58 sec) and run for 12 hr at 40,000 rpm in a SW55Ti rotor (Beclonan) at 10° C. Fractions (160 μl) were collected using the Piston Gradient Fractionator (Biocomp, Serlabo) and their absorbance at 280 nm was measured. To calibrate the gradient, standard proteins were applied to glycerol gradient and in parallel. The reproducibility of each glycerol gradient was also checked by measuring in each fraction the enzymatic activity of an endogenous marker, NDP kinase (110 kDa).

Fluorescence Analysis of Cell Extracts

Fluorescence analysis of cell extracts (2-5×$10^5$ in 150 μl) was performed using a PTI Quantamaster fluorometer with excitation wavelength of 480 nm (YFP) or 433 nm (CFP and CFP/YFP FRET) and emission/excitation bandpasses of ⅜ nm.

Results

NEMO Behaves as a Monomer in *E. coli* and in Ikkα$^{-/-}$Ikkβ$^{-/-}$ Cells

FIG. 1 shows the behavior of recombinant NEMO (rNEMO) analyzed either by gel filtration (FIG. 1A) or by glycerol gradient centrifugation (FIG. 1B), a highly reproducible technique (see FIG. 1, inset). In gel filtration, rNEMO eluted in a symmetrical peak with an apparent mass (Mr) of 500 kDa. In contrast, when analyzed by glycerol gradient centrifugation, rNEMO displayed the migrational properties of a globular protein with an apparent mass of 50 kDa indicating that the abnormal elution profile is due to the elongated shape of NEMO. We then analyzed the oligomeric state of native NEMO in Ikkα$^{-/-}$Ikkβ$^{-/-}$ cells (FIG. 1C). NEMO migrated as an asymetrical peak. The first peak (80%) corresponds to monomeric NEMO, the other one (20%) to either a homotrimer or a heterocomplex (Mr 150 kDa).

Figure 2:
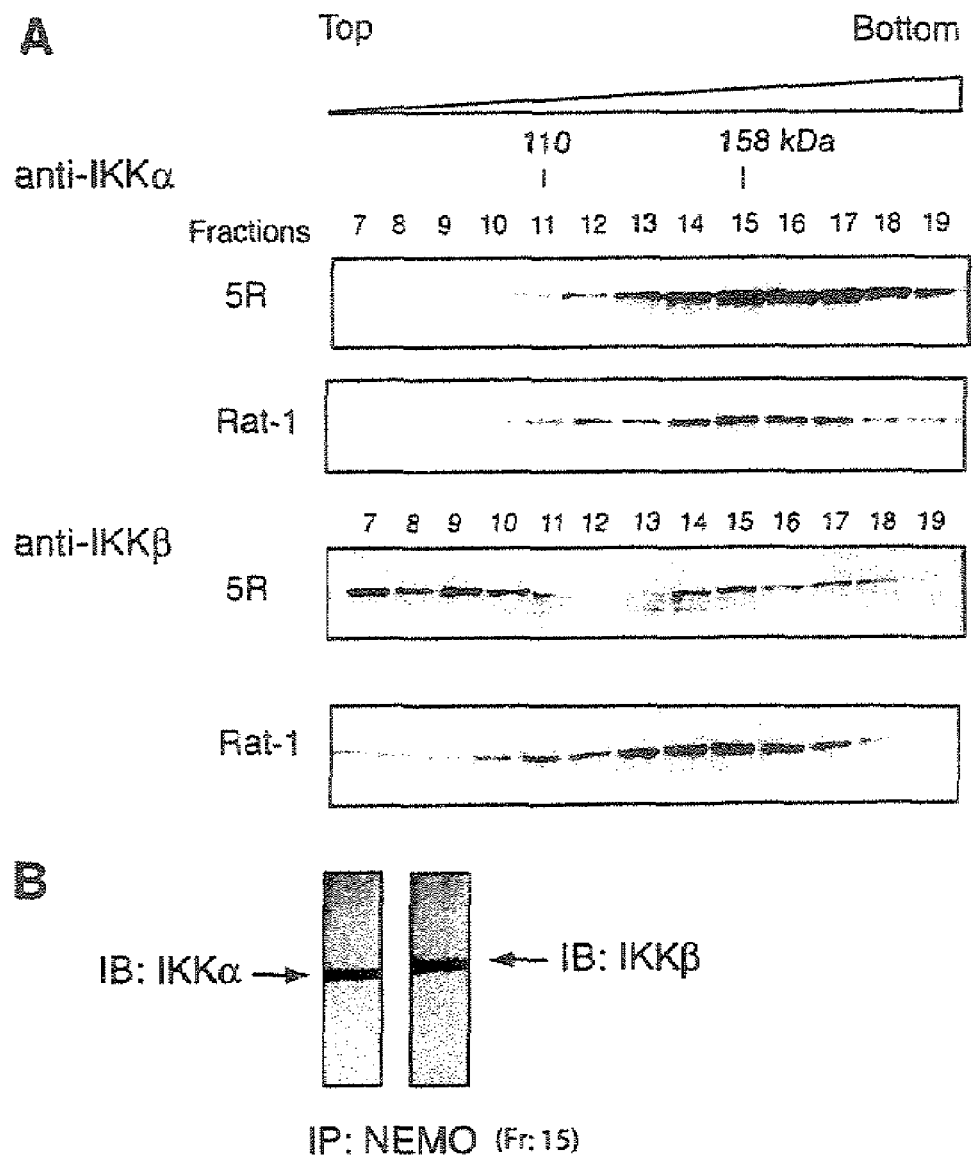
FIG. 2: Distribution of IKKα and IKKβ in glycerol gradient fractions from Rat-1 and Nemo$^{-/-}$ 5R extracts. A. WB detection of IKKα and IKKβ in glycerol gradient fractions of Rat-1 and 5R cytosolic extracts. Anti-IKKα and -IKKβ antibodies were from Imgenex. B. Immunoblotting (IB) detection of IKKα and IKKβ in NEMO immunoprecipitate (IP) of fraction 15 from Rat-1 glycerol gradient. NEMO was immunoprecipitated with anti-NEMO antibodies for 3 hr at 4° C.

Analysis of IKKs in 5R (Nemo$^{-/-}$) and Rat-1 Cell Extracts by Glycerol Gradient Centrifugation In order to better understand the role of NEMO in the assembly of the IKK complex, IKK kinases were analyzed by Western blot in glycerol gradient fractions from Rat-1 and 5R cytosolic extracts. In both extracts, IKKα was found in a complex of 140-160 kDa (FIG. 2A) corresponding to dimeric species. In contrast, in 5R cell extracts, most of IKKβ (80%) migrated as a monomer of 80 kDa (calculated Mr 86,6 kDa), and only a small amount of IKKβ (20%) was detected as dimers. The monomeric form of IKKβ was no longer present in Rat-1 cell extracts showing that the presence of NEMO induces the formation of IKKβ/NEMO heterocomplexes with a 1:1 stoichiometry. NEMO association with IKKα or IKKβ was also investigated by NEMO immunoprecipitation followed by analysis of the pull down by Western blot. As shown in FIG. 2B, NEMO pull down contained both IKKα and IKKβ. Taken together, these results suggest the existence of both IKK dimers and NEMO/IKK heterocomplexes within the 140-160 kDa protein complexes.

Oligomerization of the IKK Complex in Rat-1 and M319-5b Cells

Figure 3:
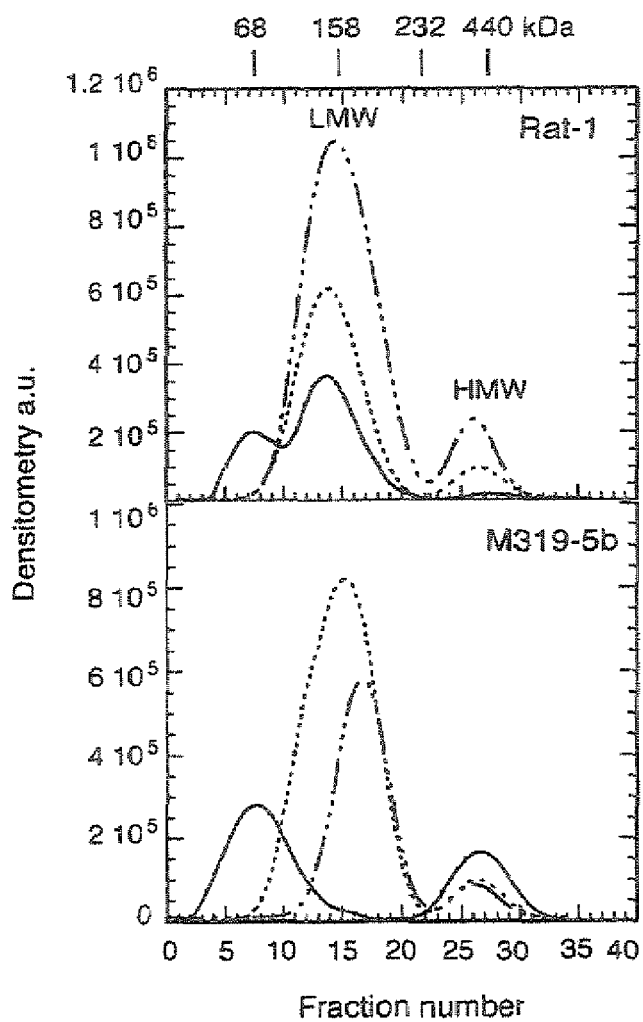
FIG. 3: Distribution and activity of the IKK complex components in glycerol gradient fractions from Rat-1 or Tax-activated M319-5b cell extracts. A. Densitometric analysis (arbitrary units) of Western blot-detected NEMO (—), IKKα(——) or IKKβ (...) in glycerol gradient fractions of Rat-1 or M319-5b cell extracts. LMW/HMW: Low and High Molecular Weight complex. B. In vitro kinase assays in LMW and HMW fractions from Rat-1 or M319-5b cells. Kinase assays (KA) were performed using wt or S32A/S36A mutant GST-IκBα substrate. $^{32}$P labelling of substrates was analyzed by SDS-PAGE, autoradiographied for 7 hr and densitometry quantified. WB:Western blot co-detection of IKKα and IKKβ. SA, specific activity is the ratio of densitometric quantification of IκB $^{32}$P labelling and Western blot IKK detection.
Figure 3:
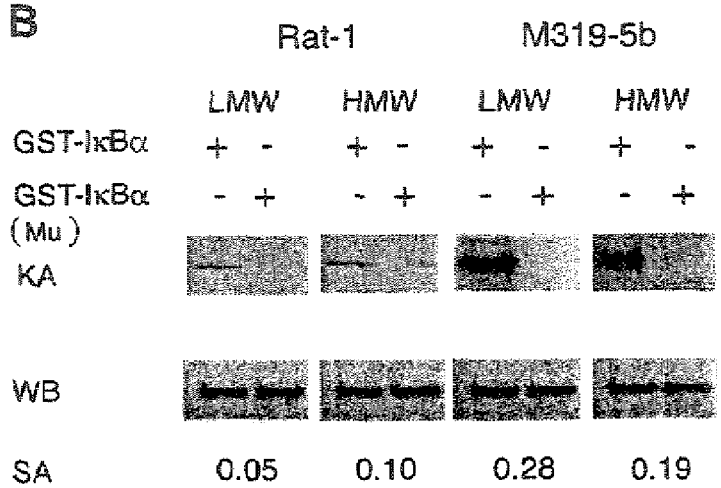

The presence of NEMO, IKKα and IKKβ in cytosolic extracts from Rat-1 and constitutively activated M319-5b cells (see supplementary data) was analyzed following fractionation on glycerol gradient (FIG. 3).

In Rat-1 cell extracts, NEMO eluted mainly in two peaks with Mr of 50 kDa and 140-160 kDa. We further call the latest the low molecular weight (LMW) complex. For IKKα and IKKβ kinases, two peaks were identified, one corresponding to LMW complex, the other one with a high (350 kDa) molecular weight (HMW) complex was associated with a minor amount of NEMO (FIG. 3A, top). Only a weak kinase activity was detected in these two molecular complexes likely reflecting basal activity (FIG. 3B).

In M319-5b cell extracts, a fraction of NEMO was again detected as a monomer, but less NEMO was found in the LMW complex, correlated with a significant recruitment into the HMW complex (FIG. 3A, bottom) and an enhancement of kinase activity (FIG. 3B). The HMW complex (≈440 kDa) was slightly shifted compared to that of Rat-1 cell extracts. In the LMW complex, IKKα elution shifted from 140-160 kDa (Rat-1) to 160-180 kDa (M319-5b) while IKKβ elution shift was less important. As NEMO was depleted in these fractions, these peaks reflected several forms of dimeric kinases. Intriguingly, a 5-fold increase in kinase activity of the LMW complex was observed compared to only a 2-fold increase for the HMW complex (FIG. 3B). We hypothesize that this shifted LMW pool corresponds to permanently activated dimeric kinases unbound to NEMO.

NEMO FRET Following IL-1β Treatment of Reconstituted Nemo$^{-/-}$MEF Cells

Figure 4:
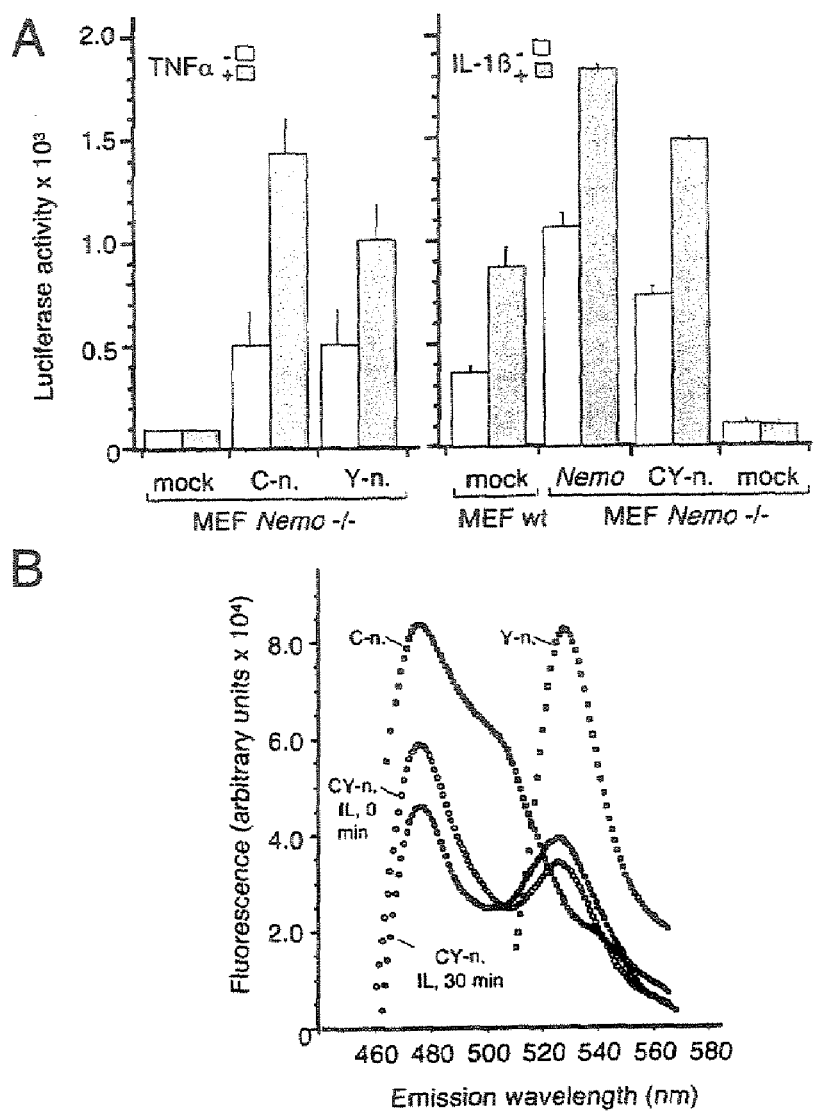
FIG. 4: IL-1β promotes FRET between CFP-NEMO and YFP-NEMO fusion proteins A. Luciferase activity resulting from IgK-luciferase reporter gene activation by TNFα or IL-1β (left or right histogram) in MEF wt cell lysates or in lysates from Nemo$^{-/-}$ MEF cells either mock treated or transfected with pECFP-Nemo (C-n.), pEYFP-Nemo (Y-n.) plasmids or with both plasmids (CY-n.). B. Emission spectra in lysates from C-n. (■), Y-n. (□) or from CY-n. cells either untreated (○; IL -0 min) or treated with IL-1β for 30 min (●; IL–30 m using excitation at 433 nm (C-n., CY-n.) or 480 nm (Y-n.). The peak emission of Y-n. was normalized to the peak emission of C-n.

Nemo$^{-/-}$MEF cells were reconstituted by transient transfection with plasmids encoding CFP- or/and YFP-NEMO fusion proteins. For Western blot analysis of cell extracts, see supplementary data. NF-κB pathway activation by TNFα in cells transfected with each of the fluorescent NEMO plasmids was rescued (FIG. 4A left panel). The activation of the pathway by IL-1 was comparable between wt and Nemo$^{-/-}$MEF cells transfected by a plasmid coding for untagged NEMO or doubly transfected with pECFP-Nemo and pEYFP-Nemo plasmids (FIG. 4A, right panel).

In FIG. 4B the emission spectra of CFP-NEMO (maximum at 475 nm) or YFP-NEMO (maximum at 525 nm) expressing cells and of pECFP- and pEYFP-Nemo doubly transfected cells are shown following excitation at 433 nm (CFP and CFP/YFP double transfectant) or 480 nm (YFP). Under the experimental conditions employed, neither YFP excitation at 433 nm nor CFP excitation at 480 nm was observed (not shown). The double transfectant displayed an emission spectrum typical of cells expressing both fluorescent fusion NEMO proteins with characteristic maxima at 475 and 525 nm. When cells were incubated with IL1-β (30 min) a decrease in intensity of the CFP emission spectrum was observed coupled with an increase in intensity of the YFP emission spectrum typical of a FRET transfer between CFP and YFP. The transfer efficiency reached 21.7% for a 30 min incubation with IL-β.

Discussion

Glycerol gradient ultracentrifugation analysis of the three main IKK complex subunits provided new insights into the NEMO-dependent mechanism of IKK activation and allowed us to observe the heterogenous composition of the IKK complex under near physiological conditions. IKK complex assembly has been studied by gel filtration in 293 T, Yeast, COS and HeLa cells where several groups observed the formation of a large complex (700-900 kDa) but most of the time under overexpression conditions. We show here that the IKK complex molecular mass measurement by gel filtration is erroneous mainly due to the abnormal hydrodynamic properties of NEMO. Similar abnormal behaviour was observed with tight NEMO:DnaK heterocomplex containing one DnaK per NEMO molecule (data not shown), indicating that this abnormal behaviour is not restricted to NEMO:IKK heterocomplexes. The other methods previously used to determine the structure of the IKK complexes including chemical cross-linking and co-IP could have been misleading since cross-linking is biased by the formation of nonspecific NEMO oligomers and co-IP does not allow quantitative determination of kinase bound to NEMO.

Surprisingly, in Ikkα$^{-/-}$Ikkβ$^{-/-}$ MEF cells, cytosolic protein fractionation by glycerol gradient centrifugation showed that endogeneous NEMO predominantly forms monomers. Similar results were previously reported with rNEMO expressed in *E. coli* (Agou, F., Ye, F., Goffinont, S., Courtois, G., Yamaoka, S., Israel, A. and Veron, M. (2002) NEMO trimerizes through its coiled-coil C-terminal domain. *J Biol Chem*, 277, 17464-17475) indicating that the monomeric state results mainly from an intrinsic property of NEMO rather than an impairment in the *E. coli* chaperone machinery. This monomeric state is unexpected because NEMO contains a long N-terminal coiled-coil domain called CC1 which is thought to form stable dimers. One possible explanation is that the N-terminal domain may form an intramolecular rather than an intermolecular coiled-coil structure like that observed in the Structural Maintenance of Chromosomes family of proteins (Haering, C. H., Lowe, J., Hochwagen, A. and Nasmyth, K. (2002) Molecular architecture of SMC proteins and the yeast cohesin complex. *Mol Cell*, 9, 773-788). When IKKα and IKKβ are present, the major fraction of NEMO co-migrates within the 140-160 kDa LMW complex, a mass which is compatible with that of NEMO/IKKβ and NEMO/IKKα complexes with 1:1 stoichiometry. The overlapping, yet slightly different, migrations between dimeric pools of kinases (5R cells), (FIG. 2A), and NEMO/IKK complexes make it difficult to determine the relative proportion of kinase/kinase and NEMO/kinase complexes in these fractions. Since the presence of NEMO induced a shift of IKKβ toward the LMW complex, it is very likely that the amount of NEMO/kinase complexes is higher than that of kinase dimers in the LMW complexes, at least for IKKβ. The fact that two distinct IKKα and IKKβ kinase complexes could be fractionated in NEMO-deficient 5R fibroblasts expressing Tax shows for the first time that IKKβ homodimers are less stable than IKKα homodimers. However, we can not rule out the possibility that this difference is promoted by the presence of Tax even if we could not detect it in the IKKα complex by Western blot.

When comparing constitutively Tax-activated and unstimulated fibroblasts, significant NEMO recruitment was observed within the ≈440 kDa IKK complex. This NEMO recruitment/oligomerization which was confirmed by FRET experiments following transient IL-1β stimulation, was observed in parallel with an increase in kinase activity of both LMW and HMW complexes. The Mr shift of kinases within the LMW complex may simply reflect an increase in the relative proportion of dimeric kinases and of NEMO/IKK heterocomplexes. The exact composition of the HMW IKK complex is nevertheless difficult to determine. Our experiments showed that it did not contain previously described components of the IKK complex such as Hsp90, TAK1 or ELKS (not shown). Furthermore, HMW IKK complex formation was specific to the Tax-dependent pathway because no similar complex was observed in transiently TNFα-activated Rat-1 cells where a 220-240 kDa complex was found (not shown). The Mr of this TNFα-dependent IKK complex composed of NEMO, IKKα and IKKβ is compatible with a subunit composition of two kinases and two NEMOs.

The results presented here reveal a dynamic assembly of the IKK complexes and the presence of a free pool of NEMO monomer provide more consistent data supporting the view that NEMO can enter into multiple protein-protein partnerships as recently reported with the ATM-NEMO (Wu, Z. H., Shi, Y., Tibbetts, R. S. and Miyamoto, S. (2006b) Molecular Linkage Between the Kinase ATM and NF-{kappa}B Signaling in Response to Genotoxic Stimuli. *Science*, 311, 1141-1146) and the PIDDosome complexes (Janssens, S., Tinel, A., Lippens, S. and Tschopp, J. (2005) PIDD mediates NF-kappaB activation in response to DNA damage. *Cell*, 123, 1079-1092) in response to DNA damage. It still remains to be determined what molecular and cellular events promote the spatiotemporal formation of NEMO oligomers in a stimulus dependent manner. Clearly, Lys63-linked ubiquitin conjugation by upstream proteins such as TRAFs and RIP proteins (Wu, et al (2006a) NEMO is a sensor of Lys 63-linked polyubiquitination and functions in NF-kappaB activation. *Nat Cell Biol*) could provide this attractive molecular basis, but awaits future analysis.

Example 2

Plasmids

The murine Nemo gene was amplified using plasmid HA-Nemo (Agou, F., et al (2002) *J Biol Chem*, 277, 17464-17475) as template (EcoR1 and BamH1 site extended primer sequences on request). The PCR product, pECFP-C1 and pEYFP-C1 plasmids (BD Biosciences) were digested by BamH1 and EcoR1 and the digested PCR product was ligated to the digested plasmids giving rise to pECFP-Nemo and pEYFP-Nemo vectors. The cfp/yfp-Nemo regions of the plasmids were sequenced to control gene integrity.

Characterization of the M319-5b Cells

Figure 5:
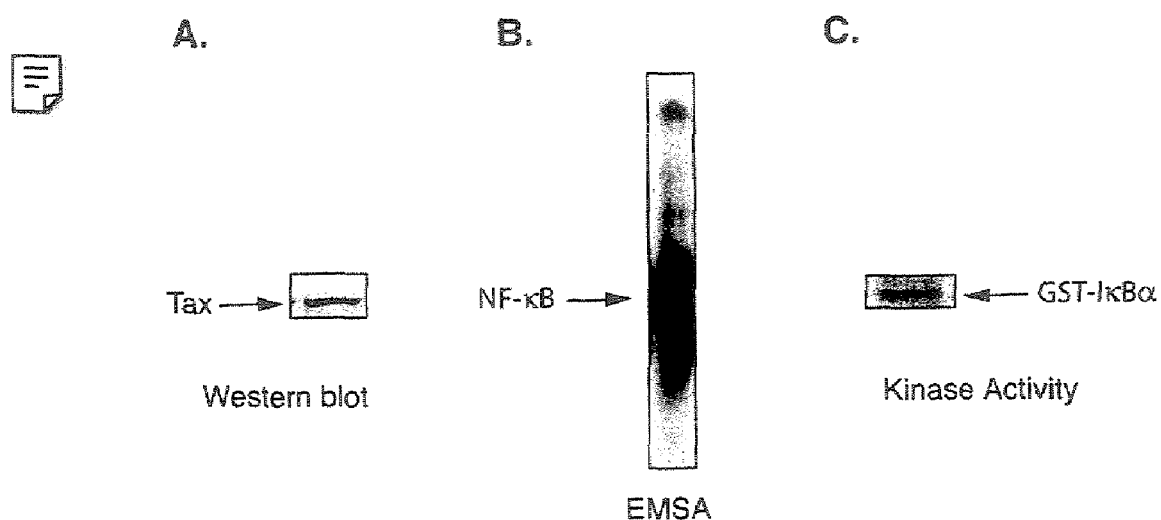
FIG. 5: M319-5b cell characterization. An extract from cytosolic M319__5b cell extract was analyzed by A. Western blotting using an anti-Tax monoclonal antibody. B. EMSA on nuclear extracts. C. Kinase assay of the cell extract was performed with the GST-IκBα protein (aa 1-54) followed by SDS-PAGE and autoradiography for 7 hr.

M319-5 cells were derived from rat fibroblast transformed by a mutant Tax protein competent to activate NF-κB. As M319-5 cells tend to loose Tax expression after extended passages in the presence of G418, stable transfection of M319-5 cells with Igκ2bsrH have been performed to confer them a NF-κB dependent blasticidin S resistance (Yamaoka, S.,et al (1998) Cell, 93, 1231-1240). The resistant M319-5 cells (M319-5b) express the Tax protein (FIG. 5A), display a high NF-κB DNA binding activity (FIG. 5B) and an IκBα kinase activity (supplementary FIG. 5C). Nuclear extracts and supershift assays were performed as described previously (Yamaoka et al. (1998) Cell, 93, 1231-1240).

Analysis of Protein Expression in pECFP- and pEYFP-Nemo Transfected Cells

Figure 6:
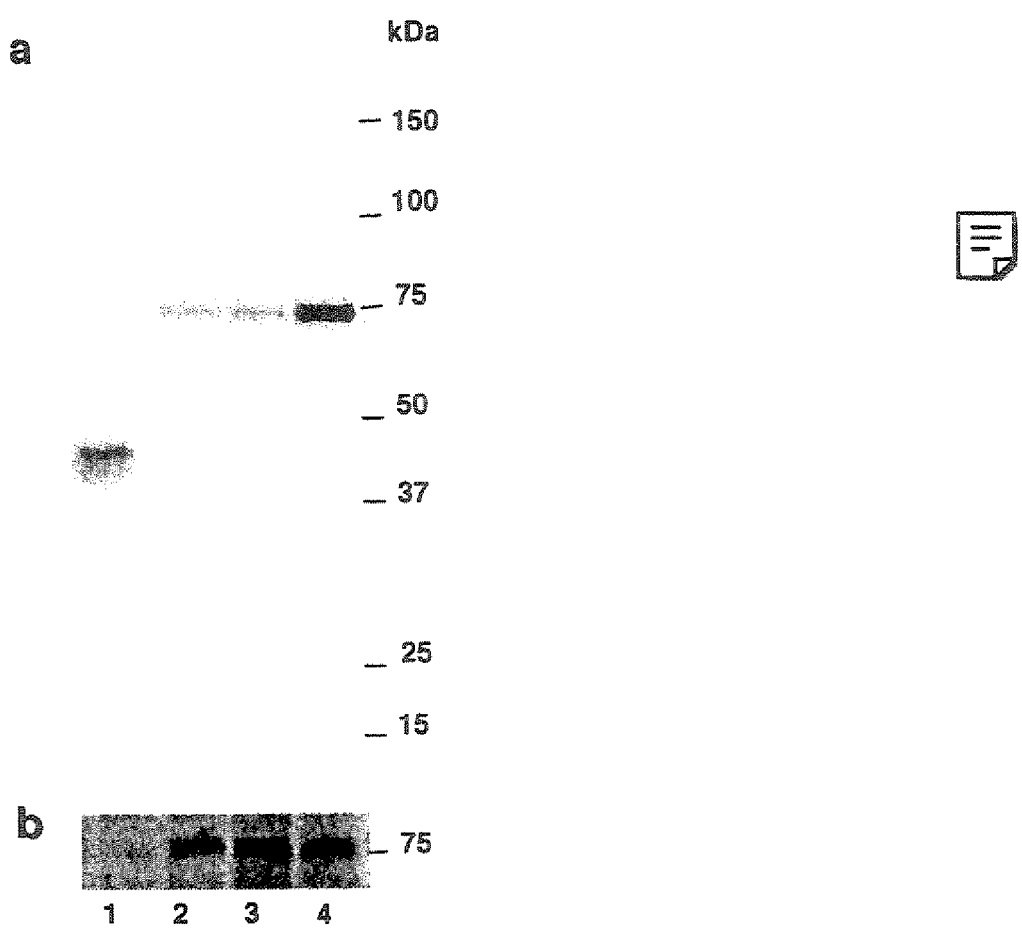
FIG. 6: Western blot analysis of CFP- and YFP-Nemo transfected cells. Western blot analysis of lysates from MEF wt (1) and from pECFP-Nemo (2), pEYFP-Nemo (3), pECFP-and pEYFP-Nemo (4) transfected Nemo$^{-/-}$ MEF cells using anti-NEMO (a) and anti-GFP antibodies (b).

A volume of clarified lysate corresponding to $1 \times 10^5$ cells in Laemmli buffer was loaded on a 3-8% Tris-acetate polyacrylamide gel which was run in denaturing conditions. Nitrocellulosis transferred proteins were analyzed by Western blot using an ECL detection system (Amersham) (FIG. 6).

Obviously, numerous modifications and variations of the present invention are possible in light of the above teachings. It is therefore to be understood that within the scope of the appended claims, the invention may be practiced otherwise than as specifically described herein.

What is claimed is:

1. A method of identifying a substance which inhibits mammalian NFκ-B Essential Modulator (NEMO) oligomerization, comprising
providing a cell deficient in endogenous NEMO, and which is transformed with one or more polynucleotides that express at least two peptides that comprise a NEMO oligomerization region wherein the NEMO oligomerization region is at least one of coiled-coil motif or zinc finger moiety of the C-terminal domain of mammalian NEMO;
applying the substance to the cell; and
analyzing the level of oligomerization of the peptides that comprise a NEMO oligomerization region compared to the level of oligomerization of the peptides in the absence of the substance, wherein a reduction of oligomerization of the peptides in the presence of the substance indicates that the substance inhibits NEMO oligomerization wherein analyzing the level of oligomerization comprises a Fluorescence Resonance Energy Transfer protocol.

2. The method of claim 1, wherein the at least two peptides each comprise a detectable moiety.

3. The method of claim 2, wherein the detectable moiety is a fluorescent moiety.

4. The method of claim 2, wherein the fluorescent moiety is a fluorescent polypeptide.

5. The method of claim 4, wherein the fluorescent polypeptide is one or more of a green fluorescent protein, cyan fluorescent protein, and a yellow fluorescent protein.

6. The method of claim 2, wherein the at least two peptides comprise at least two different detectable moieties.

7. The method of claim 6, wherein the detectable moieties are fluorescent moieties.

8. The method of claim 7, wherein the fluorescent moieties are fluorescent polypeptides.

9. The method of claim 8, wherein the fluorescent polypeptides are a green fluorescent protein, cyan fluorescent protein, or a yellow fluorescent protein.

10. A method of identifying a substance which inhibits mammalian NFκ-B Essential Modulator (NEMO) oligomerization, comprising transforming a cell deficient in endogenous NEMO with one or more polynucleotides that express at least two peptides that comprise a NEMO oligomerization region wherein the NEMO oligomerization region is at least one of coiled-coil motif or zinc finger moiety of the C-terminal domain of mammalian NEMO;

applying the substance to the transformed cell; and analyzing the level of oligomerization of the peptides that comprise a NEMO oligomerization region compared to the level of oligomerization of the peptides in the absence of the substance, wherein a reduction of oligomerization of the peptides in the presence of the substance indicates that the substance inhibits NEMO oligomerization wherein analyzing the level of oligomerization comprises a Fluorescence Resonance Energy Transfer protocol.

11. The method of claim 10, wherein the at least two peptides each comprise a detectable moiety.

12. The method of claim 11, wherein the detectable moiety is a fluorescent moiety.

13. The method of claim 11, wherein the fluorescent moiety is a fluorescent polypeptide.

14. The method of claim 13, wherein the fluorescent polypeptide is one or more of a green fluorescent protein, cyan fluorescent protein, and a yellow fluorescent protein.

15. The method of claim 11, wherein the at least two peptides comprise at least two different detectable moieties.

16. The method of claim 15, wherein the detectable moieties are fluorescent moieties.

17. The method of claim 16, wherein the fluorescent moieties are fluorescent polypeptides.

18. The method of claim 17, wherein the fluorescent polypeptides are a green fluorescent protein, cyan fluorescent protein, or a yellow fluorescent protein.

* * * * *